United States Patent
Thouément et al.

(10) Patent No.: US 11,779,695 B2
(45) Date of Patent: Oct. 10, 2023

(54) INSTRUMENT USED IN SURGERY AND IRRIGATING OF THE INSTRUMENT

(71) Applicant: KARL STORZ SE & Co. KG, Tuttlingen (DE)

(72) Inventors: Yann Thouément, Les Essarts-le-Roi (FR); Régis Besse, Le Perray-en-Yvelines (FR); Daniel Kärcher, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 302 days.

(21) Appl. No.: 16/739,646

(22) Filed: Jan. 10, 2020

(65) Prior Publication Data
US 2020/0222622 A1 Jul. 16, 2020

(30) Foreign Application Priority Data
Dec. 16, 2019 (EP) ..................... 19216485

(51) Int. Cl.
| | | |
|---|---|---|
| *A61M 3/02* | (2006.01) | |
| *A61M 39/12* | (2006.01) | |
| *A61B 17/3201* | (2006.01) | |
| *A61B 17/29* | (2006.01) | |
| *A61M 39/10* | (2006.01) | |
| *A61M 39/16* | (2006.01) | |

(52) U.S. Cl.
CPC .......... *A61M 3/0279* (2013.01); *A61B 17/29* (2013.01); *A61B 17/3201* (2013.01); *A61M 39/10* (2013.01); *A61M 39/12* (2013.01); *A61M 39/16* (2013.01)

(58) Field of Classification Search
CPC .... A61M 3/0279; A61M 39/10; A61M 39/12; A61M 39/16; A61B 17/29; A61B 17/3201
See application file for complete search history.

(56) References Cited

U.S. PATENT DOCUMENTS

| | | | |
|---|---|---|---|
| 5,408,991 A | 4/1995 | Iida | |
| 2001/0033806 A1* | 10/2001 | Stanley | ................... C23F 11/10 134/22.12 |
| 2020/0015839 A1* | 1/2020 | Eastwood | ........ A61B 17/00234 |

OTHER PUBLICATIONS

Ioanovici, T Extended European Search Report; Application No. 19218812.6-1113, dated Apr. 8, 2020, , pp. 1-7, Munich.
DPMA Search Report, Munich Germany, dated Oct. 24, 2019, Application No. 10 2019 100 601.5.

* cited by examiner

*Primary Examiner* — Brooke Labranche
(74) *Attorney, Agent, or Firm* — Honigman LLP

(57) ABSTRACT

An instrument configured for performing a surgery includes a distal end portion, a proximal end portion, and a tube connecting the distal end portion and the proximal end portion. A fluid fitting includes an inlet configured for receiving flow of an irrigating fluid into the instrument and at least two exits configured for guiding the flow of the irrigating fluid out of the instrument. A first exit is configured to allow the irrigating fluid to flow towards the distal end portion of the instrument and a second exit is configured to allow the irrigating fluid to flow towards the proximal end portion of the tube. A size of the first exit is larger than a size of the second exit to enable greater flow towards the distal end portion.

11 Claims, 2 Drawing Sheets

INSTRUMENT USED IN SURGERY AND IRRIGATING OF THE INSTRUMENT

FIELD

The present invention relates to an instrument used in surgeries and in particular to the irrigating of the inside of said instrument.

BACKGROUND

These instruments are used in many kinds of surgeries like endoscopy, laparoscopy, and neurosurgery.

In recent years, brain tumors are removed by surgery by means of endoscopy (neuroendoscopy). In such cases, brain surgery is performed by making a very small opening in the skull. An instrument attached to the endoscope is introduced in this small opening and surgery is performed. The instrument comprises forceps and/or scissors at the distal end. Some kinds of tumors like pituitary tumors can be removed by introducing an instrument attached to the endoscope through the nose.

During this surgery, the instrument is applied to remove the tumor and hence, blood, tissues and other debris enter into the inner part of the instrument. Hence, after the surgery, the inner part of the instrument is in a contaminated state with the blood, tissues and debris from surgery.

This instrument is reusable and hence, it is very much required to irrigate the inner part of the instrument after the surgery thoroughly along the entire length of the endoscope tube.

To irrigate the instrument tube properly, an irrigating fluid is introduced in instrument tube through the fluid fitting. But sometimes due to the position of the fluid fitting and length of instrument, distal end of the instrument tube is not properly irrigated, and more efforts are required to irrigate the distal part of the tube. In this case, most of the irrigating fluid escapes through the proximal part of the instrument.

Hence, the object of this present invention is to provide solution to the problem of irrigating distal part of the instrument tube.

SUMMARY

This object is achieved by providing, instrument configured for performing a surgery comprising a distal end portion, a proximal end portion, a tube connecting the distal end portion and the proximal end portion, and a fluid fitting comprising an inlet for entering irrigating fluid inside the instrument and two exits configured for guiding the flow of the irrigating fluid in the instrument, wherein a first exit is configured to allow the irrigating fluid to flow towards proximal distal end of instrument and second exit is configured to allow irrigating fluid to flow towards distal proximal end of the instrument tube, characterized in that, a size of the first exit is larger than the size of second exit.

Larger exit allowing irrigating fluid to flow towards distal end of instrument tube allows more irrigating fluid to flow in the direction of distal part as compared to proximal part. Also, for ease of operation during surgery, instrument is so constructed that tube of instrument is bended at distal side of instrument.

BRIEF DESCRIPTION OF THE DRAWINGS

Examples of the execution of the invention are shown in more detail in the drawing and are explained in more detail in the following description.

DETAILED DESCRIPTION

Figure 1:
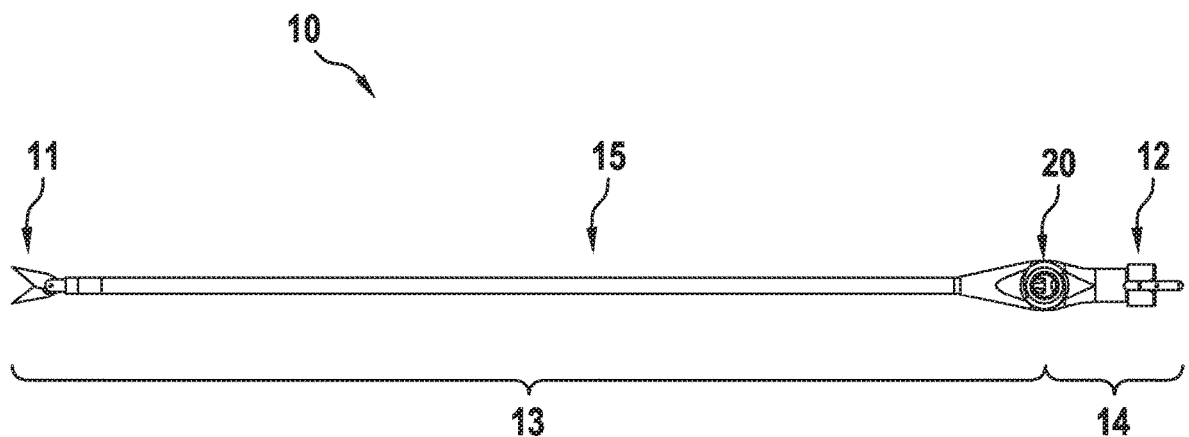
FIG. 1 is a top view of the whole instrument

FIG. 1 shows the top view of the whole instrument 10. The instrument comprises a proximal end portion 12 and a distal end portion 11. A tube 15 is attached between the proximal end portion 12 and the distal end portion 11. On the distal end portion 11, forceps or scissors are attached to perform the surgery. The proximal end portion 12 of the instrument 12 can be attached to a handle (not shown) to perform surgery.

Figure 3:
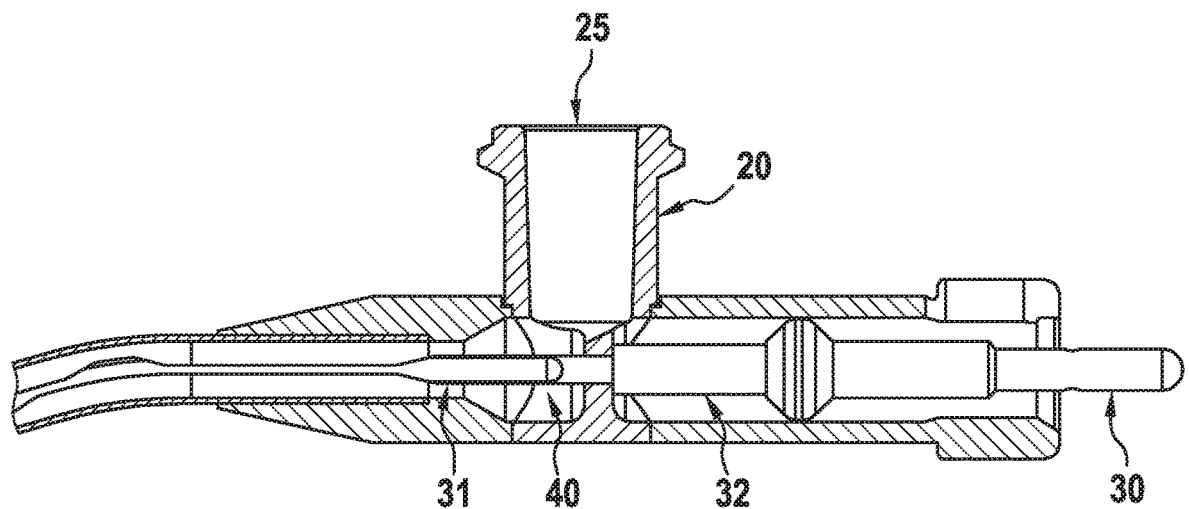
FIG. 3 is a section view of the instrument and fluid fitting

A fluid fitting 20 is connected to a proximal part of the instrument 10 near to proximal end portion 12. The close view of the fluid fitting 20 is shown in FIG. 3 and construction of the fluid fitting 20 is described with the help of FIGS. 3, 4 and 5.

Irrigating fluid is injected through the fluid fitting 20 which flows to proximal and distal parts of the instrument 10. From the Figures, it is clear that distal part 13 of the instrument 10, which needs to be irrigated from inside of tube 15, is longer than the proximal part 14 of instrument 10, which also needs to be irrigated from inside, Hence, it is difficult to irrigate the distal part 13 of instrument entirely.

Figure 2:
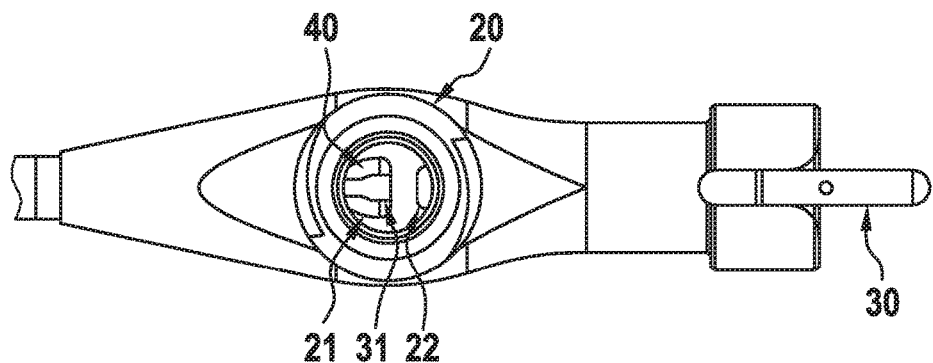
FIG. 2 is a top view of the fluid fitting connected to instrument

FIG. 2 shows close-up top view of the fluid fitting 20 and proximal part 14 of the instrument 10. As shown in the Figure, two exits 21 and 22 are provided at a lower part of the fluid fitting 30 and couple with the instrument 10 where the proximal part 14 and distal part 13 meet. From these exits, irrigating fluid flows towards two opposite directions. First exit 21 is provided such that irrigating fluid flows in the direction of distal part 13 of the instrument tube 15, Second exit 22 is provided such that irrigating fluid flows in the proximal part 14 of the instrument 10. As it can be clearly seen in the Figure, first exit 21, which allows irrigating fluid to flow towards the distal end portion 11 of the instrument 10 is larger in size as compared to second exit 22, which allows irrigating fluid to flow towards the proximal end portion 12 of the instrument 10.

Due to difference in the size of the two exits 21 and 22, more irrigating fluid flows towards the distal end portion 11 of instrument tube 15 compared to the irrigating fluid flowing towards the proximal end portion 12 of the instrument 10. This creates more pressure at the distal part 13 of the instrument 10. This building of pressure in the distal part 13 of the instrument 10 helps the irrigating fluid to flow towards the distal end portion 11 of the instrument tube 15. This causes irrigating of the entire length of the inside of the instrument tube 15.

FIG. 3 shows a two-dimensional cross-section view of the instrument 10 and particularly of the fluid fitting 20. The fluid fitting 20 is connected to the instrument 10 at a proximal side near to the proximal end portion 12. After surgery, for irrigating the instrument tube 15, irrigating fluid is inserted from inlet 25 of fluid fitting 20. As two exits 21, 22 are provided for output of the fluid fitting 20, part of the irrigating fluid flows towards the distal end portion 11 of the instrument 10 through the first exit 21 and part of the irrigating fluid flows towards the proximal end portion 12 of the instrument 10 through the second exit 22. This irrigating fluid then flows through the inside 40 of the instrument tube 15 irrigating the inside of the tube. This irrigating fluid washes the blood, tissues and debris accumulated in the instrument tube 15 during surgery.

Push rod 30 is provided from the proximal end portion 12 to the distal end portion 11 of the instrument 10. Irrigating fluid flows in the instrument tube 15 around the push rod 30 irrigating push rod 30 from outside. Spring 32 is provided in the proximal part of push rod 30 for operating the push rod 30 during surgery. Irrigating fluid also irrigates this spring 32.

Figure 4:
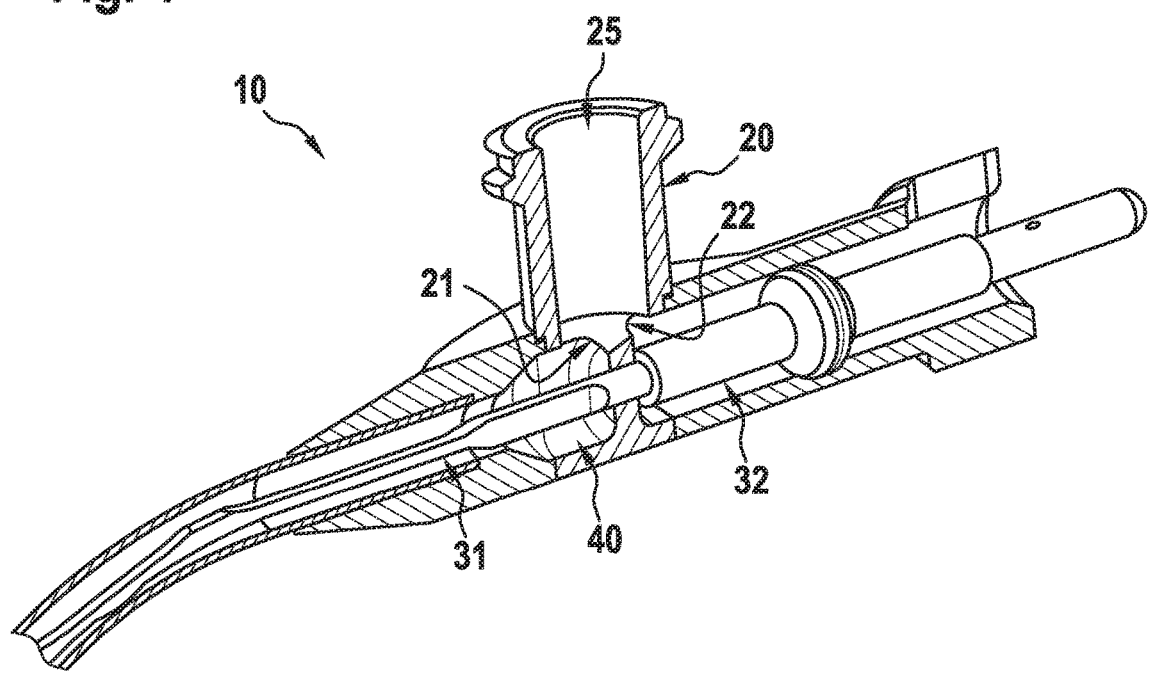
FIG. 4 is an isometric section view of the instrument and fluid fitting

FIG. 4 shows isometric view of a cross-section of the instrument 10 and the fluid fitting 20. From the isometric view, it is clearer the construction of the fluid fitting 20, the push rod 30, and the instrument tube 15. As already described according to FIGS. 1-4, instrument 10 comprises the fluid fitting 20 connected to the proximal side of the instrument 10 and the fluid fitting 20 is divided into two exits 21 and 22 so that when irrigating fluid is inserted in the inlet 25 of the fluid fitting 20, first exit 21 allows irrigating fluid to flow in the direction of the distal end and the second exit 22 allows irrigating fluid to flow in the direction of the proximal side, irrigating the inside 40 of the instrument tube 15 and outside of the push rod 30 and spring 32.

Though the current embodiment of present invention describes fluid fitting with two exits allowing irrigating fluid to flow at proximal and distal part of instrument, it is clear to the person skilled in the art that more than two exits can be provided to the fluid fitting to irrigate further parts of the instrument if needed.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An instrument configured for performing a surgery comprising:
   a distal end portion;
   a proximal end portion;
   a tube connecting the distal end portion and the proximal end portion;
   a fluid fitting, the fluid fitting being an elongated member orthogonal to the tube, the fluid fitting comprising an inlet configured for receiving flow of an irrigating fluid into the instrument and an outlet fluidly connected to and opposite of the inlet, the outlet including a first exit and a second exit, the first exit and the second exit completely separated from each other by a wall, the wall dividing the opening so as to guide the flow of irrigating fluids into the first exit and towards the distal end portion of the instrument and into the second exit and towards the proximal end portion of the instrument; and
   a push rod extending from the distal end portion to the proximal end portion within the tube, wherein the push rod is enclosed by the wall.

2. The instrument of claim 1, wherein a size of the first exit is larger than a size of the second exit to enable greater flow towards the distal end portion.

3. The instrument of claim 1, wherein the fluid fitting is connected to a proximal side of the instrument near to the proximal end portion of the instrument.

4. The instrument of claim 1, wherein the instrument is further configured for performing neurosurgery.

5. The instrument of claim 4, wherein a proximal end of the fluid fitting encloses the push rod.

6. The instrument of claim 5, wherein the distal end portion includes scissors.

7. The instrument of claim 5, wherein the distal end portion includes forceps.

8. The instrument of claim 1 wherein the fitting is connected to a proximal side of the instrument near to the proximal end portion of the instrument.

9. The instrument of claim 1, wherein the push rod is configured for performing neuro surgery.

10. A fluid fitting for coupling an irrigation system to an instrument for neurosurgery, the instrument including a tube having a distal end portion and a proximal end portion, the fluid fitting comprising:
    a fitting, the fitting being an elongated member orthogonal to the tube, the fitting including a proximal end configured to couple with the irrigation system and a distal end configured to couple with the instrument;
    an inlet in the proximal end of the fitting configured for receiving flow of an irrigating fluid from the irrigation system into the instrument;
    an outlet opposite of and fluidly connected to the inlet, the outlet including a first exit, a second exit and a wall dividing the first exit from the second exit so as to completely separate the first exit from the second exit, and wherein the first exit is configured to allow the irrigating fluid to flow towards a the distal end portion of the instrument, and the second exit configured to allow the irrigating fluid to flow towards the proximal end portion of the instrument; and
    a push rod extending from the distal end portion to the proximal end portion of the tube, wherein the push rod is enclosed within the wall.

11. The instrument of claim 10, wherein a size of the first exit is larger than a size of the second exit to enable greater flow towards the distal end portion.

* * * * *